(12) United States Patent
Dunagan (10) Patent No.: US 7,497,838 B1
(45) Date of Patent: Mar. 3, 2009

(54) METHOD FOR AERATING A CAST (76) Inventor: Rick D. Dunagan, 8455 Terrapin Trail, Colorado Springs, CO (US) 80919-4550

( * ) Notice: Subject to any disclaimer, the term of this patent is extended or adjusted under 35 U.S.C. 154(b) by 0 days.

(21) Appl. No.: 11/726,787

(22) Filed: Mar. 23, 2007

Related U.S. Application Data (62) Division of application No. 10/939,683, filed on Sep. 13, 2004, now Pat. No. 7,229,425.

(60) Provisional application No. 60/502,882, filed on Sep. 12, 2003.

(51) Int. Cl.
A61F 5/00 (2006.01)
A61F 13/00 (2006.01)
A61F 13/06 (2006.01)

(52) U.S. Cl. ............... 602/14; 602/3; 602/5; 602/6; 602/13; 602/60; 602/61

(58) Field of Classification Search ............ 602/1–3, 602/5–6, 10, 13, 20, 60–61; 607/108, 112; 604/307; 307/1–3, 5–6, 10, 13, 20, 60–61
See application file for complete search history.

(56) References Cited

U.S. PATENT DOCUMENTS

| | | | |
|---|---|---|---|
| 3,477,427 A | 11/1969 | Lapidus | |
| 3,561,435 A | 2/1971 | Nicholson | |
| 3,656,477 A | 4/1972 | Thomas et al. | |
| 3,701,349 A | 10/1972 | Larson | |
| 3,888,242 A | 6/1975 | Harris et al. | |
| 3,998,220 A | 12/1976 | Cleer, Jr. et al. | |
| 4,194,041 A | 3/1980 | Gore et al. | |
| 4,308,862 A | 1/1982 | Kalmar | |
| 4,387,710 A | 6/1983 | Beatty, III | |
| 4,753,241 A | 6/1988 | Brannigan et al. | |
| 4,898,160 A | 2/1990 | Brownlee | |
| 5,195,948 A | 3/1993 | Hill et al. | |
| 5,527,265 A | 6/1996 | McKeel | |
| 5,636,382 A | 6/1997 | Chopko et al. | |
| 5,916,184 A | 6/1999 | McKeel | |
| 6,027,465 A | 2/2000 | Scholz et al. | |
| 6,053,882 A | 4/2000 | Johansen | |
| 6,120,469 A | 9/2000 | Bruder | |
| 6,132,835 A | 10/2000 | Scholz et al. | |
| 6,461,379 B1 | 10/2002 | Carson et al. | |
| 6,491,034 B1 | 12/2002 | Gunaratnam et al. | |
| 6,547,751 B1 | 4/2003 | Barberio | |

(Continued)

OTHER PUBLICATIONS

Cast Care PROCEL Cast Liner, Feb. 2000 by W. L. Gore & Associates.

Primary Examiner—Patricia M Bianco
Assistant Examiner—Brandon Jackson
(74) Attorney, Agent, or Firm—Price, Heneveld, Cooper, DeWitt & Litton, LLP (57) ABSTRACT A method and apparatus for aerating a fracture sight that employs a membrane or covering that wraps and seals the outside of a breathable, orthopedic cast and typically includes an array of spaced apart protrusions on an inside surface to facilitate generally even airflow, thereby providing comfort and/or improved hygiene for the patient when an air moving device is connected to the apparatus and the air moving device is powered on.

35 Claims, 6 Drawing Sheets

U.S. PATENT DOCUMENTS 6,616,622 B1 9/2003 Barberio
6,814,079 B2 11/2004 Heaton et al.
6,945,944 B2 * 9/2005 Kuiper et al. ................ 602/13

* cited by examiner

METHOD FOR AERATING A CAST

CROSS-REFERENCE TO RELATED APPLICATIONS

This application is a divisional application of U.S. patent application Ser. No. 10/939,683, filed on Sep. 13, 2004, entitled METHOD AND APPARATUS FOR AERATING A CAST, now U.S. Pat. No. 7,229,425, which claims the benefit of U.S. Provisional Application Ser. No. 60/502,882, filed Sep. 12, 2003, entitled CAST COOLING DEVICE. The disclosures of both U.S. patent application Ser. No. 10/939,683 and U.S. Provisional Application Ser. No. 60/502,882 are hereby incorporated by reference in their entirety.

BACKGROUND OF THE INVENTION

The present invention generally relates to orthopedic casts, and more particularly, to the ventilation of orthopedic casts.

The use of casts for immobilizing a broken limb is well known. Casts are typically worn for many weeks until the broken limb heals. However, there is no effective way of washing and/or aerating the skin immediately underlying the cast and, after a period of time, dirt and bacteria can buildup under the cast creating skin irritation and/or odors. Additionally, typical fracture casts are made from plaster and/or resin impregnated bandage material. This casting material is activated by water and is applied while wet over a cast padding material which encircles the fracture sight. The casting material undergoes a curing process and becomes rigid, thereby immobilizing the fractured bone. However, these casts have the tendency to remain damp for indefinite periods of time. Not only is there the initial water used for activating the cast material, but there is also the patient's perspiration that works up through the cast padding to become absorbed by the cast. Add to this the natural tendency of casting material to be hydroscopic, and this can be an acute problem for those who live in damp or humid climates. A damp cast is both uncomfortable and unhygienic. The warm, moist environment of a cast is ideal for the production of infection-causing bacteria and other microorganisms. It is possible to reduce this skin irritation, odor, and/or possible infection by circulating air between the cast and skin.

A variety of different structures and methods have been proposed in the past for providing air ventilation to a patient's skin under a surgical, fractural, or orthopedic cast. For example, it is known to provide various venting devices which are positioned either underneath the casting material or through the casting material to promote the flow of air from within the casting material. Because these devices are positioned between the skin and the cast, such devices are usually installed or constructed by nurses, doctors, or other health care professionals during the fabrication of the cast. Therefore, additional steps and/or devices must be included and/or taken by the orthopedic physician during the wrapping of the initial casting material, thereby requiring additional time and/or material. Further, these prior art devices, methods, and systems do not create a uniform circulation. As a result, certain areas within the cast get too much air flow and generally are much cooler while other areas get too little air flow and remain moist and warm feeling to the cast wearer.

Therefore, a significant need exists for an easily manufacturable, retrofitable cast ventilating device which is easy to use and provides for a more substantially uniform airflow within the cast that can be applied and used by the patient without involvement or effort by the physician.

SUMMARY OF THE INVENTION

An embodiment of the present invention includes a ventilation device for application to the outside of a breathable orthopedic cast that includes a covering that includes an inlet adapted to receive an air moving device and where the covering is adapted to sealingly enclose an outside surface of an orthopedic cast made at least in part from a breathable casting material such that when the cast is enclosed in the covering and the air moving device is attached to the inlet, once air is moved by the air moving device, an airflow is established between an inside surface of the cast and the outside surface of the cast.

Another embodiment of the present invention includes a method of ventilating an orthopedic cast. The method includes providing an air moving device and a covering including an inlet adapted to engage an air moving device; sealingly enclosing the covering to an outside surface of a breathable orthopedic cast; connecting the air moving device to the inlet; and utilizing the air moving device to move air between an inside surface of the cast and the outside surface of the cast, through the breathable casting material.

DETAILED DESCRIPTION OF THE PREFERRED EMBODIMENTS

Figure 1:
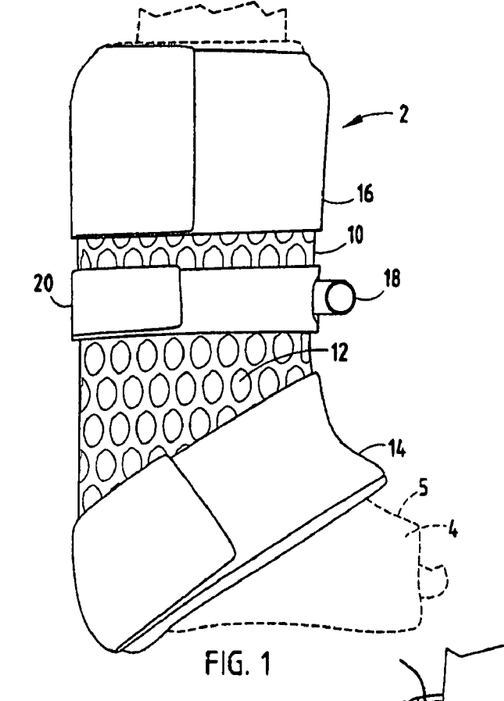
FIG. 1 is an elevated front view of an embodiment of the cast aerating device of the present invention shown installed on an orthopedic leg cast.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification, are exemplary embodiments of the inventive concepts defined in the appended claims. Hence, specific dimensions and other physical characteristics relating to the embodiments disclosed herein are not to be considered as limiting, unless the claims expressly state otherwise.

The term "elastomeric membrane" as used herein is meant to describe a preferred embodiment of the invention wherein the membrane is preferably stretchable. However, the invention is not meant to be so limited and non-stretchable or non-elastomeric, membranes can also be utilized. Additionally, the preferred embodiment of the present invention is meant to be utilized with a breathable casting material. As used herein, a breathable casting material is meant to describe a casting material, which either due to the porosity of the material itself or to due to features disposed therein, such as apertures, allows air to be drawn through the casting material. One such breathable orthopedic cast material that may be used is the casting material disclosed in U.S. Pat. Nos. 6,027,465 and 6,132,835, the disclosures of which are hereby incorporated by reference in their entirety. Typically, the breathable cast material is lined with a liner material such as PROCEL®, which is a waterproof, breathable cast padding from W. L. Gore & Associates, Inc. of Flagstaff, Ariz.

A cast aerating device according to an embodiment of the present invention (FIG. 1), typically includes a non-porous, typically elastomeric, membrane 10 that wraps around and seals an outside surface 4 of an orthopedic cast and typically includes an array of spaced-apart ridges or bumps 12 disposed on the inside, cast-facing surface of membrane 10. Bumps 12 typically operate to facilitate an even distribution of airflow within and through orthopedic cast 5. Typically, a non-porous elastomeric membrane 10 sealingly engages to the outside surface 4 of cast 5. In one embodiment, this is accomplished using straps 14 and 16, which sealingly engage elastomeric membrane 10 and the opposite ends of cast 5. An inlet 19 is typically disposed generally centrally within membrane 10. The air moving device may be secured over the inlet utilizing an adapter a strap 20. The vacuum or other air moving device is typically attached and/or otherwise engaged with inlet 19 utilizing adapter 18, but a direct connection may also be used. Typically, the adapter is positioned inlet 19 disposed in membrane 10 and is typically sealingly engaged against the outside surface of membrane 10, thereby ensuring a generally leak proof seal. The air moving device typically includes a nozzle that engages a second end of the adapter that is not engaged to the membrane. The air moving device typically applies a vacuum or suction which enables air or other gas, typically air that is less moist than the air between the cast and skin, to be drawn through the cast ends. Optionally, the air or gas may be cooler than ambient air. The air moving device circulates air within the cast and causes air to pass through the casting material. This causes the cast material to release any accumulated moisture and cools the patient's skin, typically through use of the lower than ambient air or gas or evaporation of moisture. In general, this airflow typically provides a means for aeration at the fracture sight which not only significantly enhances healing and comfort, but also typically precludes moisture-induced cast deterioration and prevents infection.

Figure 2:
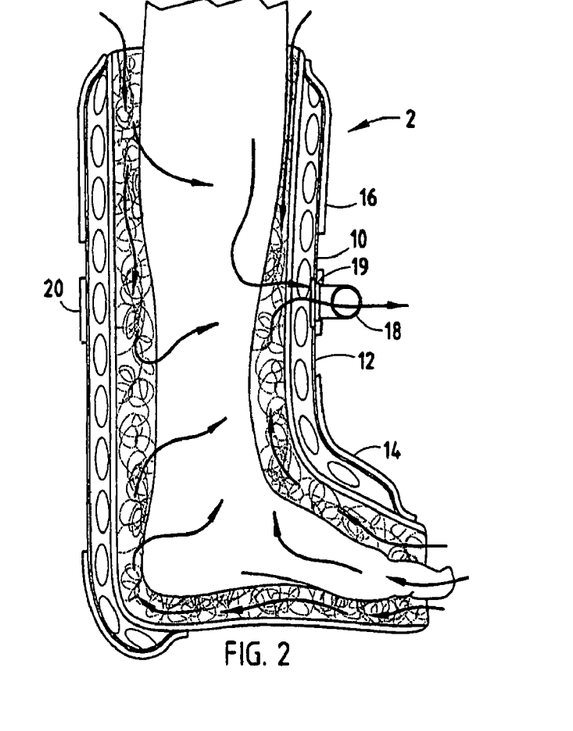
FIG. 2 is a cross-sectional view of the aerating device of FIG. 1.

Elastomeric membrane 10 of the present invention is particularly well suited for use over an orthopedic cast which utilizes a porous casting material. The elastomeric membrane 10 in conjunction with a breathable casting material allows elastomeric membrane 10 to be sealed along its ends utilizing straps 14 and/or 16, such that when a vacuum or other air moving source is engaged, air can be circulated through all areas of the cast. When one location is utilized to supply air flow from an air moving device, the velocity near inlet 19 is higher than the more diffuse air flow. Accordingly, the inside, cast-facing surface of the elastomeric membrane typically contains protrusions that typically decrease in surface density and/or size (see FIGS. 8-9) the further they are from the inlet. Ridges and/or bumps 12/12C of membrane 10 are typically used to modify the air flow along the orthopedic cast in a manner which typically enables all areas of the orthopedic cast to have a sufficient airflow inside of the cast, through the casting material, and to the outside of the cast as illustrated in FIG. 2. By obstructing air flow in certain areas of the cast and not obstructing airflow in other areas, bumps 12/12C can also optionally be tailored to provide a customized airflow within the cast by preventing and/or removing areas within the cast that receive too much or too little air flow.

Figures 3, 4:
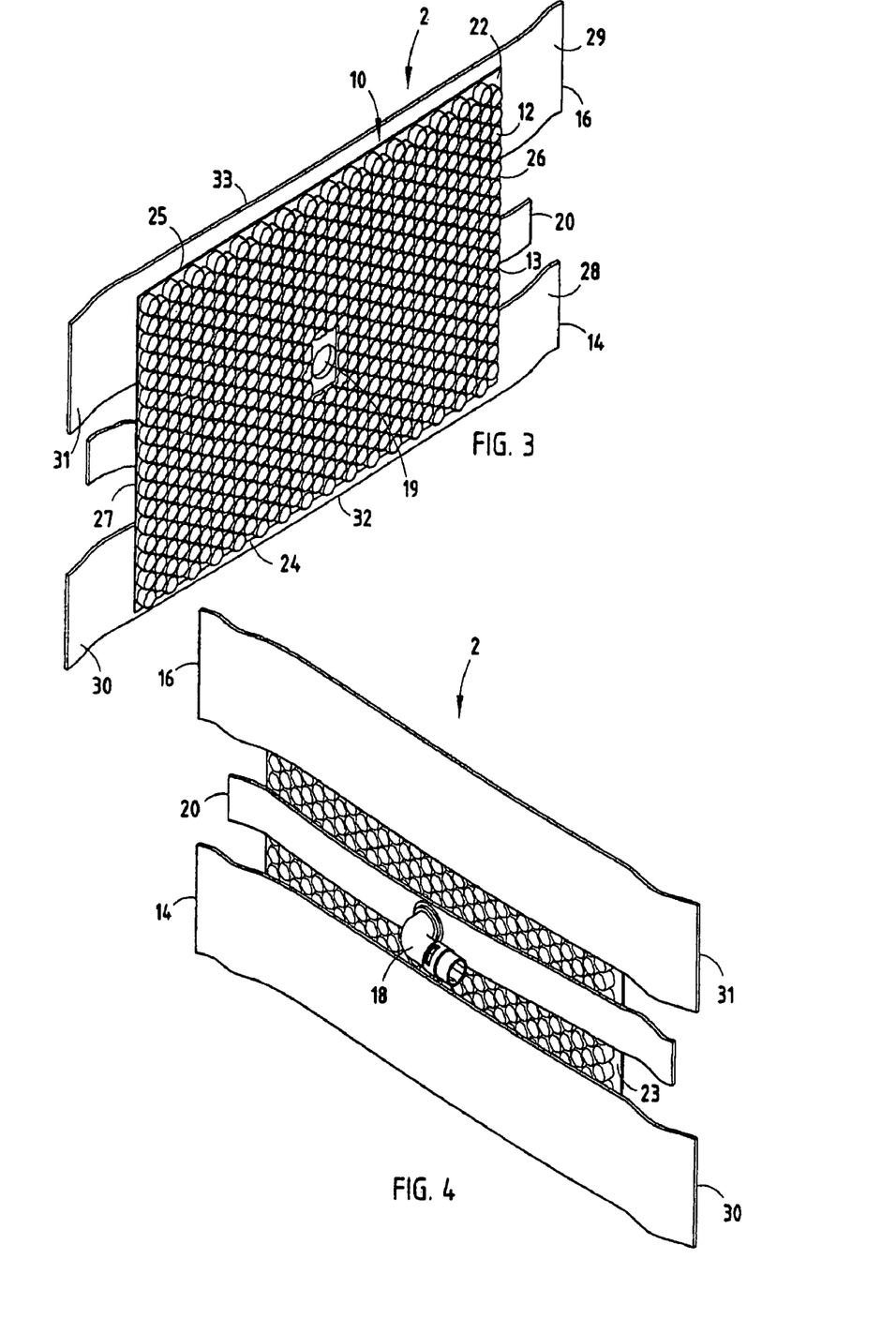
FIG. 3 is a perspective view of the aerating device in an uninstalled state, illustrating an inside, cast-facing surface of an embodiment of the present invention.
FIG. 4 is a perspective view of the aerating device illustrating an outside surface of an embodiment of the present invention.

With respect to FIGS. 3 and 4, cast aerating device 2 is illustrated detached from an orthopedic cast 5 and includes an inside, cast-facing surface 22 (FIG. 3) and an opposite, outside surface 23 (FIG. 4). As discussed above, the inside surface typically includes a plurality of ridges, bumps or the like 12 which provide a plurality of channels 13 therebetween. In use, when membrane 10 is securely and sealingly engaged around the exterior surface of orthopedic cast 5, channels 13 provide an avenue from which air is passed through. By providing raised surfaces 12, the airflow through the porous cast material is typically more evenly distributed throughout the entire circumference, width, and/or length of the orthopedic cast thereby facilitating receipt of adequate airflow and offering ventilation to areas of the user's appendage. This configuration also typically ensures that clean, dry air is being drawn through the casting material resulting in the release of moisture from more areas of the patient's skin.

Non-porous membrane 10 may be fabricated from numerous materials. Generally, any material, typically an elastomeric material, can be used such that membrane 10 may be wrapped around the exterior surface of an orthopedic cast. Such materials are commonly known within the art and may include, but are not limited to plastics, elastomers, silicons, rubbers, and the like. Typically, a non-porous polyethylene is used. Non-porous membrane 10 may be fabricated utilizing two non-permeable polyethylene sheets wherein a first layer of polyethylene sheeting is laminated to a second layer of polyethylene sheeting creating a plurality of "bubbles" or raised surfaces therebetween. The "bubbles" are created by having pockets of air trapped between the two polyethylene sheets. Such a membrane is commonly known as "bubble wrap." Alternatively, a non-porous membrane may be molded, cast, or fabricated with numerous techniques or processes.

Straps 14 and 16 or other securing device may be used. However, typically, straps 14 and 16 are employed and are typically disposed on a first end 24 and a second end 25 of membrane 10 and extend outwardly from opposite edges 26 and 27. Straps 14 and 16 are typically engaged or otherwise adhered to an outside surface 23 of membrane 10 such that straps 14 and 16 extend beyond opposite edges 26 and 27, as well as extend beyond first end 24 and second end 25. In this manner, when membrane 10 is wrapped around the outside 4 of orthopedic cast 5, a portion 28 of strap 14 and a portion 29 of strap 16, or a second portion 30 of strap 14 and a second portion 31 of strap 16, respectively, will wrap around and/or secure itself to the opposite corresponding portion of straps 14 and 16 thereby securing the membrane to the outside of the orthopedic cast. Further, overhung edges 32 and 33 of straps 14 and 16, respectively, typically sealingly engage the outside surface 4 of orthopedic cast 5 thereby creating a sealed environment wherein elastomeric membrane 10 is optimally sealed to provide airflow only from the opposite ends of the sealed membrane cast assembly as illustrated in FIG. 2. Further, a strap 20 may optionally also be provided to aide in the retention of membrane 10 to the orthopedic cast.

Straps 14 and 16 may be fabricated from numerous materials. Generally, a flexible and/or elastomeric material is used such that straps 14 and 16 may be wrapped around the outside of an orthopedic cast. Ends 28 and 29 may be secured or otherwise affixed to ends 30 and 31, respectively, using a variety of fasteners, systems, and/or mechanisms. For example, a hook and loop type fastening mechanism may be used as well as buttons, snaps, or the like. Typically, straps 14 and 16 are made from an elastic material which is self-adhering such that ends 28 and 29 overlappingly adhere to ends 30 and 31 by "clinging" and do not require an additional fastening method.

The additional embodiments described hereafter will denote similar parts with the corresponding earlier referenced reference numerals, except for a different alphabetical notation. Identical components will be referred to by identical reference numerals.

Figure 5:
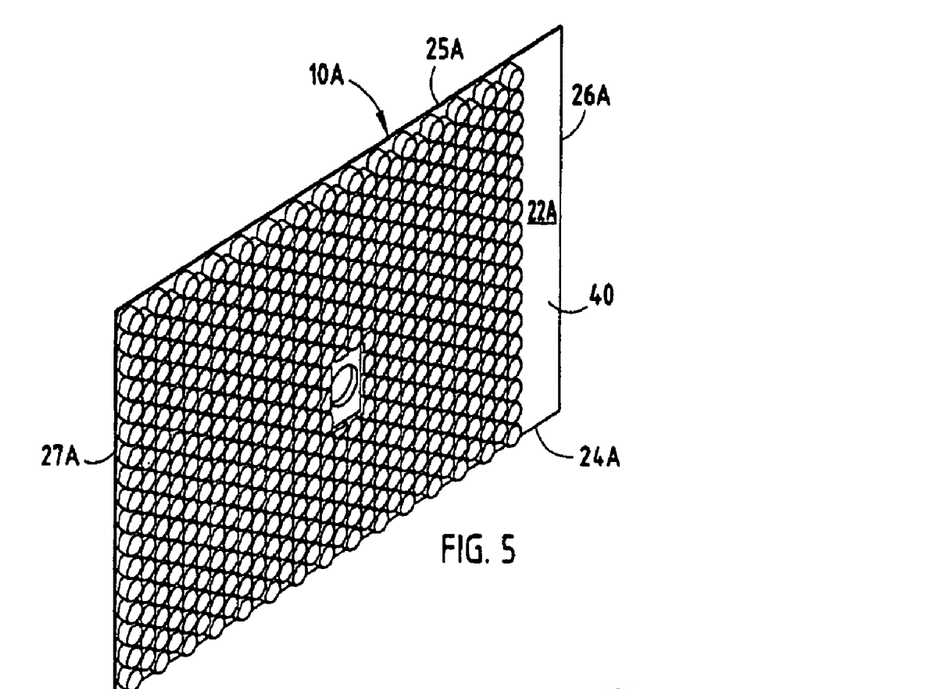
FIG. 5 is a perspective view of another embodiment of the aerating device, illustrating an inside, cast-facing surface.
Figure 6:
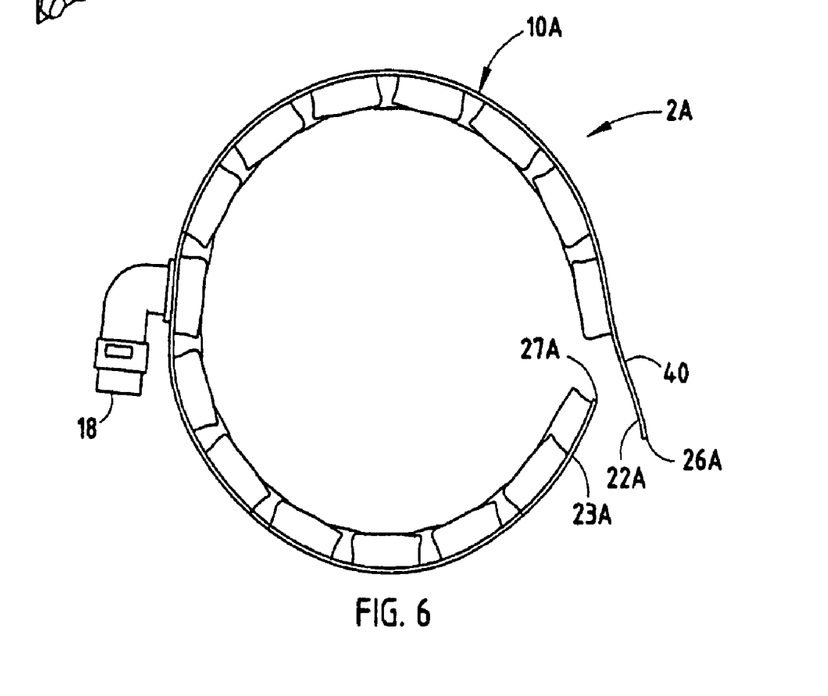
FIG. 6 is a top view of the aerating device of FIG. 5 shown in a partially installed configuration.

Another embodiment of the cast aerating device 2A includes a non-porous membrane having an integral closure flap 40. In membrane 10A, a closure flap 40 is disposed along an edge 26A. Closure flap 40 is typically used in place of straps 14 and 16 and/or 20 to securely retain membrane 10A on orthopedic cast 5. With respect to FIG. 6, closure flap 40 of end 26A will sealingly engage opposite end 27A thereby simultaneously retaining membrane 10A on the outside of an orthopedic cast as well as sealing ends 26A and 27A. In this embodiment, end sections 24A and 25A (FIG. 5) remain unsealed to allow air to flow through. As described with regard to straps 14, 16, and/or 20, closure flap 40 may engage opposite end 26A using a variety of closing fasteners, systems, and/or mechanisms. However, typically membrane 10A utilizes the above-described self-clinging material or a hook and loop type fastening mechanism, thereby allowing the inside, cast-facing surface 22A of membrane 10A to be adhered to or cling to the outside surface 23A on or near end 27A.

Yet another embodiment of the cast aerating device 2B of the present invention (FIG. 7) includes a non-porous membrane 10B. Membrane 10B typically includes a continuous flange 50 disposed along its periphery, opposite edges 26B and 27B and first and second ends 24B and 25B, respectively. As described above with regard to membrane 10, opposite edges 26B and 27B overlappingly secure one another, thereby sealingly retaining membrane 10B to an outside of an orthopedic cast. In addition, the portion of flange 50 disposed along first and second ends 24B and 25B, sealingly engages the outside of the orthopedic cast to provide a typically air tight configuration to membrane 10B.

Figure 8:
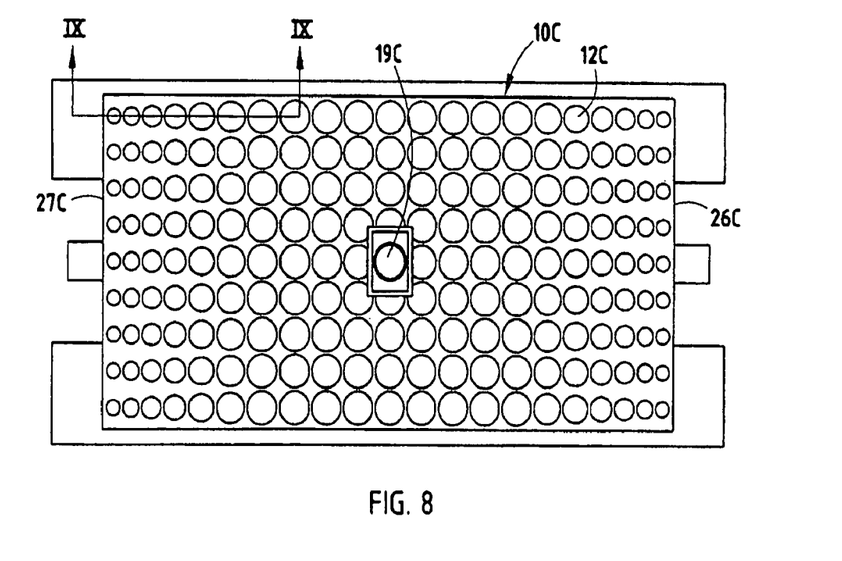
FIG. 8 is an elevated, front view of an inside, cast-facing surface of another embodiment of the aerating device.
Figure 9:
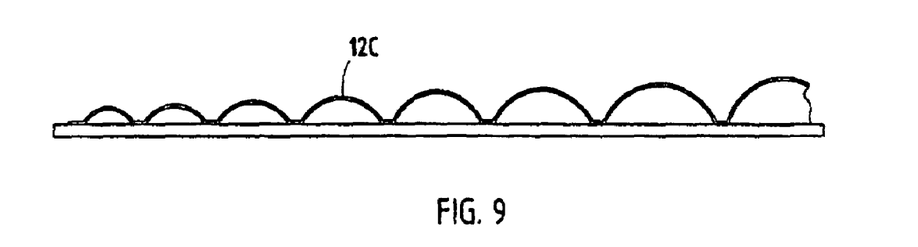
FIG. 9 is a partial, cross-elevated sectional view of the aerating device of FIG. 8 taken along line IX-IX.

Another embodiment of the cast aerating device 2C of the present invention (FIG. 8) includes a non-porous membrane 10C having protrusions 12C which vary in volume. In membrane 10C, protrusions 12C are smaller in size (FIGS. 8-9) with respect to the protrusion's volume at opposite edges 26C and 27C and increase in volume as the protrusions get closer to inlet 19C. Typically, membrane 10C includes a plurality of circular protrusions 12C which may vary in circumference and height from edges 26C and 27C as they tend towards inlet 19C as illustrated in FIGS. 8 and 9. This further facilitates substantially uniform airflow by maintaining a more steady airflow throughout the surface of the cast. This is achieved by greater air flow area near the inlet and as generally decreased airflow area the further the site is from the inlet.

Figure 10:
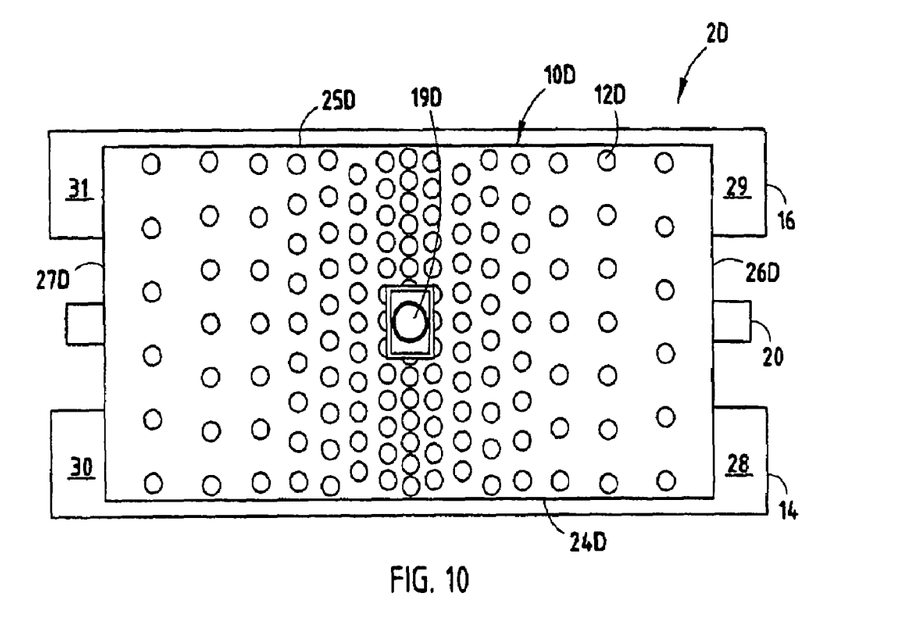
FIG. 10 is an elevated view of the inside, cast-facing surface of another embodiment of the aerating device.

Another embodiment of the cast aerating device 2D of the present invention (FIG. 10) includes a non-porous membrane 10D having protrusions 12D that vary in spatial density. Of course, the volume and spatial density may both be varied. In membrane 10D, protrusions 12D vary in special density from a decreased spatial density along edges 26D, 27D, and outside edges 24D and 25D, and increase in spatial density as protrusions 12D tend towards inlet 19D. Of course, it is envisioned that the volume and/or area of protrusions 12C can simultaneously be varied along with the spatial density to come up with additional embodiments as the specific requirements dictate. As discussed above, by varying the number of protrusions, their size (volume), and/or their spatial density, the device may be configured to facilitate a more even or a customized air flow. However, the protrusions' characteristics discussed above may conceivably be modified as described to establish a more pronounced air flow or decrease the air flow throughout the cast or through a particular portion of the cast; however, this is not typical.

Figure 7:
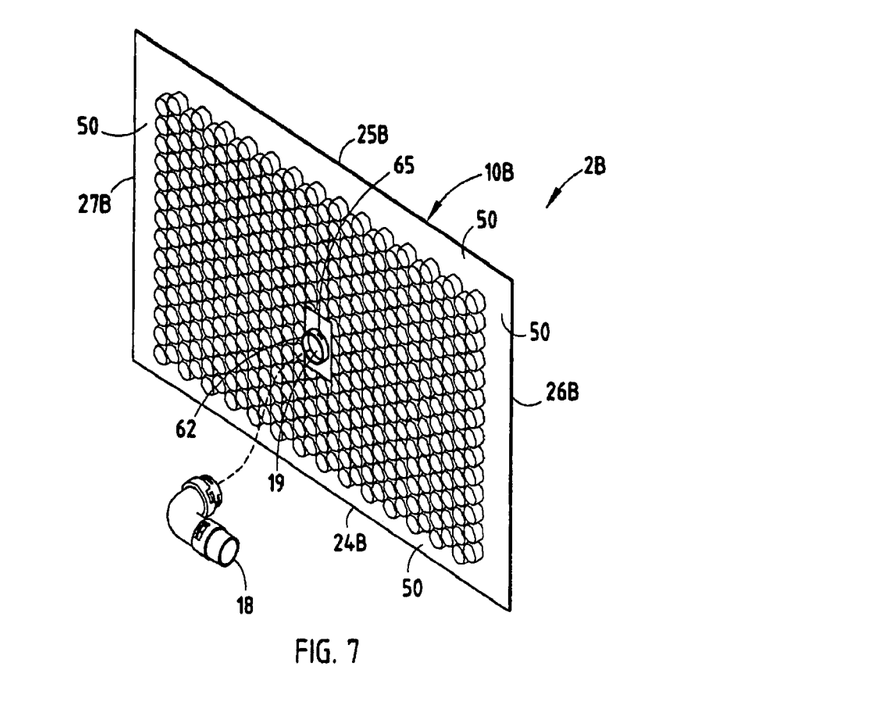
FIG. 7 is a perspective view of an outside surface of another embodiment of the aerating device.
Figures 11, 12:
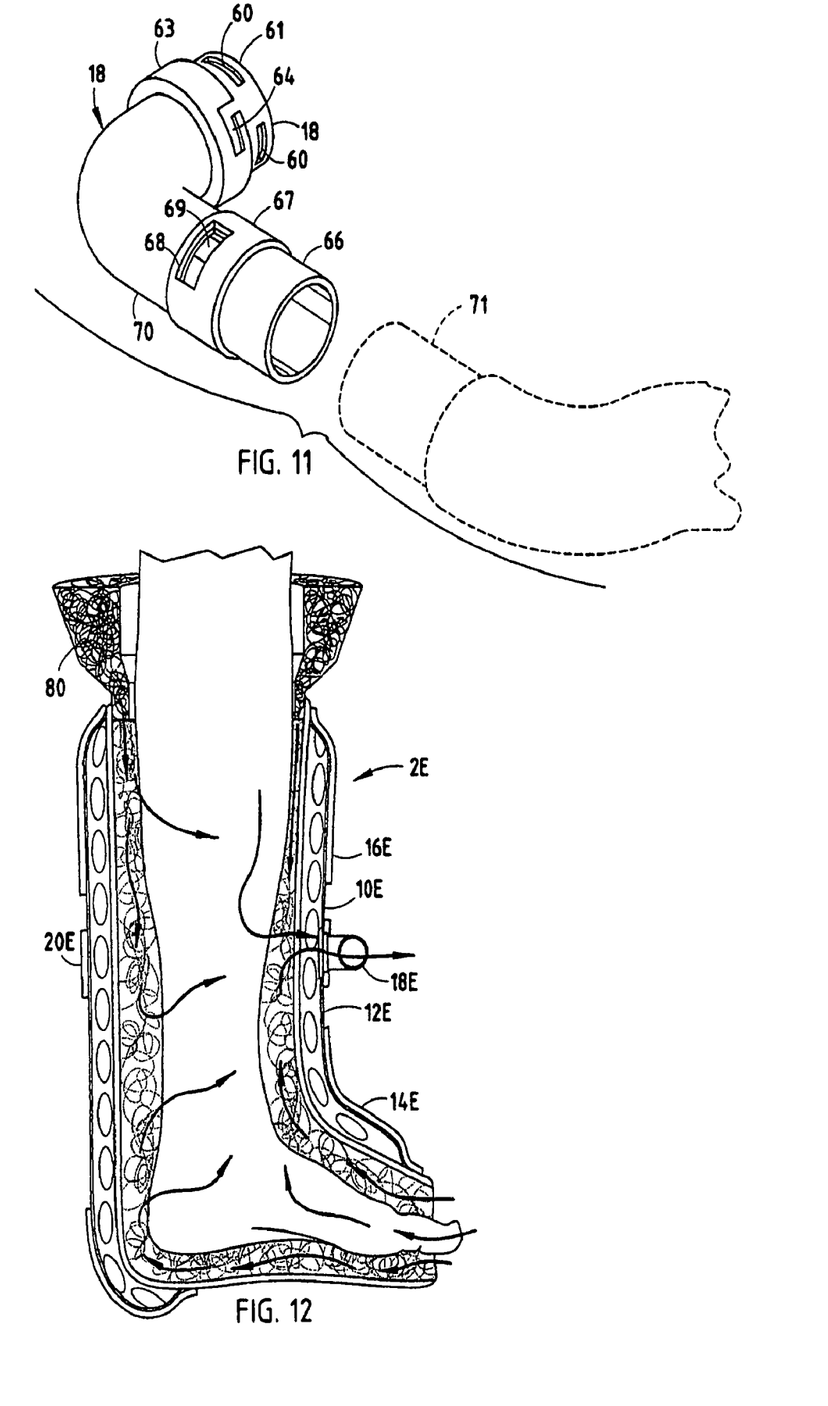
FIG. 11 is a perspective view of an adapter assembly according to an embodiment of the present invention.
FIG. 12 is a cross-sectional view of another embodiment of the cast aerating device shown installed on an orthopedic leg cast.

FIGS. 7 and 11 adapter 18 typically includes a plurality of openings 60 disposed on an inlet end 61 which is adapted to be inserted through a flange or other similar mating surface 62 disposed over inlet 19 in membrane 10. End 61 typically further includes a fastening ring 63 typically having a locking mechanism 64 disposed thereon. Locking mechanism or slot 64 is typically adapted to be releasably engaged with tab 65 of flange 62 thereby releasably securing adapter 18 to membrane 10 over inlet 19. Second end 66 of adapter 18 is typically adapted to be connected to an air moving device, typically a vacuum 71. Typically, a rotatable valve 67 having an opening 68 is disposed proximate to end 66 and rotatably covers an opening 69 in body 70 of adapter 18 thereby allowing the adjustment of the attached air supply or vacuum 71.

The slots 60 disposed within end 61 of adapter 18 may take on various configurations and are designed such that when adapter 18 is connected to membrane 10, openings 60 will allow air to be moved therethrough even if one or more openings 60 and/or end 61 is blocked, such as for example, by the outside cast material. This configuration ensures that in varied circumstances at least a portion of one or more openings 60 are free to allow the passage of air therethrough.

A reference numeral 10E (FIG. 12) generally designates another embodiment of the present invention having a porous and/or filtering material 80 attachable to the open ends of the orthopedic cast. FIG. 12 shows the porous and/or filtering material attached to one end of the cast, but the material 80 may also optionally be attached to the other end of the cast instead of or in addition to being attached to the end of the cast as shown. In this embodiment, membrane 10E covers an orthopedic cast as described with respect to the previous embodiments. However, a device that attaches to either open end (or both ends) of the orthopedic cast enables the introduction of a scented additive or disinfectant, via porous material 80, such that the air being discharged from the orthopedic cast would not contain any odors. Alternatively or in addition to the additive(s) disclosed above, porous material 80 may utilize a medicament or other "active" ingredient. For example, an antibiotic could be impregnated into the porous or foam-like material thereby surrounding the patient's limb with a medication or other active ingredient. In this manner an antibiotic, ointment, anti-itch, or other "active" ingredient can be continually supplied to the patient's limb without the need for removing the orthopedic cast. Additionally, when membrane 10E is applied to the outside of the orthopedic cast, the "active" ingredient and/or other additive will be aided in its dispersion and/or distribution through the casting material to be evenly distributed therethrough as previously described.

In yet another embodiment (not shown), the air supply 71, which will usually supply either a positive or negative pressure of ambient air to or through the casting material via membrane 10 may be replaced with an apparatus that provides a fluid material, typically a gaseous and/or liquid material, to and through the porous casting material thereby "bathing" the patient's limb in the gaseous and/or liquid solution. For example, it is envisioned that a gaseous active ingredient such as an antibiotic, anti-itch, or other medication can be delivered through supply 71 in an effort to treat various afflictions that the patient may have without removal of the cast. Therefore, if the patient's limb gets infected or afflicted with some other disorder, the membrane 10 can be used to sealingly enclose the orthopedic cast and a medication such as an antibiotic can be pumped through adapter 18E thereby "bathing" the patient's limb with the antibiotic or other medication. Of course, this process can be reversed such that supply 71 is a vacuum source thereby drawing in the aforementioned active ingredients through the open ends of the orthopedic cast.

As best illustrated in FIGS. 1 and 3, membrane 10 is typically used by first wrapping the membrane around an orthopedic cast such that opposite edges 26 and 27 either abut or overlappingly engage. In various preferred embodiments of the present invention, at least opposite ends 26 and 27 are thereby sealingly engaged and most preferably first and second ends 24 and 25 are also sealingly engaged to the orthopedic cast. As described with regard to the previous embodiments, this can be accomplished in various manners, however, with respect to FIG. 1, straps 14 and 16 are utilized to both retain membrane 10 in a wrapped configuration around the orthopedic cast as well as having overhung edges 32 and 33 sealingly engage the orthopedic cast, thereby retaining membrane 10 in an overlapping configuration through the overlapping engagement of ends 28, 29, 30, and 31. Further, a strap 20 may also optionally be utilized to aid in the retention and/or sealing of membrane 10. An adapter for connecting an air or other fluid moving device to the elastomeric membrane is then typically affixed to inlet 19 disposed generally centrally on outside surface 23 of membrane 10, wherein an end 66 is then attached to an air supply 71. Conceivably, while not typical, the air or other fluid moving device can be directly connected to the elastomeric membrane without the use of an adapter such as adapter 18. Adapter 18 also typically rotates while maintaining its connection with both the membrane and the air or other fluid moving device. This allows the cast wearer to move the immobilized appendage while the device is in use without interrupting air flow. Once membrane 10 sealingly engages to the orthopedic cast, the air flow device is powered or otherwise turned on to initiate an airflow therethrough. Typically, a vacuum is used to move air as illustrated in FIG. 2; air is drawn in through the open ends of the orthopedic cast and generally uniformly distributed over the patient's limb by being drawn through the porous cast material through channels 13 in membrane 10 and out through adapter 18.

The aforementioned membrane provides a method and apparatus for aerating a fracture sight that employs a membrane that wraps and seals the outside of an orthopedic cast and includes an array of spaced apart protrusions on an inside surface to facilitate generally even airflow thereby providing comfort and/or improved hygiene for the patient. Thus, an improved aeration device is provided which relieves a cast wearer's discomfort and helps prevent infection or other medical complications typically associated with wearing immobilizing casts. The apparatus is easily applied and just as easily removed from the orthopedic cast providing a simple, convenient, and effective orthopedic aeration device and method for aerating an orthopedic cast immobilized site.

In the foregoing description, it will be readily appreciated by those skilled in the art that modifications may be made to the invention without departing from the concepts disclosed herein. Such modifications are to be considered as included in the following claims, unless the claims by their language expressly state otherwise.

The invention claimed is:

1. A method of ventilating an orthopedic cast comprising:
   providing a covering comprising an inlet adapted to engage an air moving device;
   sealingly engaging the covering to an outside surface of a rigid, breathable orthopedic cast; and
   moving air between an inside surface of the rigid, breathable orthopedic cast and the outside surface of the cast, through a portion of the rigid, breathable casting material covered by the covering and also moving air through the inlet.

2. The method of claim 1 further comprising the steps of engaging an air moving device to the inlet and utilizing the air moving device to move air between the inside surface of the rigid, breathable orthopedic cast and the outside surface of the cast through the rigid, breathable casting material.

3. The method of claim 1, wherein the covering is a non-porous material and further comprises a first and a second cover end adapted to sealingly engage a first orthopedic cast end of the orthopedic cast and a second orthopedic cast end of the orthopedic cast.

4. The method of claim 1, wherein the covering comprises a plastic covering.

5. The method of claim 1, wherein the covering comprises a molded, plastic covering.

6. The method of claim 2, wherein the covering comprises an elastomeric material.

7. The method of claim 1, wherein the covering comprises an elastomeric membrane.

8. The method of claim 7, wherein the membrane comprises an inner, cast-facing surface and an outer surface, and wherein the inner, cast-facing surface wraps around the first and second outside cast ends and at least partially around the opposite outer, cast-facing surface to sealingly engage the first and second orthopedic cast ends.

9. The method of claim 1, wherein the covering sealingly engages the cast using a mechanism, wherein the mechanism comprises a self-clinging material or a hook and loop style fastening system.

10. The method of claim 1, wherein the covering comprises an edge and an opposite edge and a closure flap along the edge of the covering that sealingly engages the opposite edge of the covering.

11. The method of claim 10, wherein the closure flap along the edge uses a mechanism chosen from the group consisting of a self-clinging material and a hook and loop style fastening system to sealingly engage the opposite edge of the covering.

12. The method of claim 2, wherein the covering comprises an inner, cast-facing surface comprising a plurality of protrusions disposed thereon and an outer surface.

13. The method of claim 12, wherein the protrusions increase in size as the protrusions are spaced closer to the inlet.

14. The method of claim 12, wherein the protrusions increase in density as the protrusions are spaced closer to the inlet.

15. The method of claim 12, wherein the protrusions are spaced such that a substantially uniform airflow is maintained throughout the cast when air is moved between the inside surface of the rigid, breathable orthopedic cast and the outside surface of the cast, through the rigid, breathable casting material.

16. The method of claim 12, wherein the first cover end and the second cover end of the covering are free of the protrusions.

17. The method of claim 12, wherein the plurality of protrusions include protrusions of different sizes.

18. The method of claim 17, wherein the plurality of protrusions are non-uniformly distributed across the inner, cast-facing surface.

19. The method of claim 17, wherein the plurality of protrusions are uniformly distributed across the inner, cast-facing surface.

20. The method of claim 12, wherein the plurality of protrusions are of uniform size.

21. The method of claim 20, wherein the plurality of protrusions are non-uniformly distributed across the inner, cast-facing surface.

22. The method of claim 20, wherein the plurality of protrusions are uniformly distributed across the inner, cast-facing surface.

23. The method of claim 12, wherein the plurality of protrusions are uniformly distributed across the inner, cast-facing surface.

24. The method of claim 12, wherein the plurality of protrusions increase in spatial density as the protrusions are spaced closer to the inlet.

25. The method of claim 2, wherein the inlet is disposed about midway between the first and second cover end.

26. The method of claim 25, wherein the covering further comprises a flange adapted to engage an adapter wherein the adapter engages the flange and the air moving device.

27. The method of claim 26, wherein the air moving device comprises a nozzle comprising at least one slot and wherein the nozzle engages the adapter.

28. The method of claim 1, wherein the covering further comprises at least one pair of fastening straps that comprise a hook and loop style fastening system.

29. The method of claim 1, further comprising a nozzle for engaging an air moving device, wherein the nozzle comprises a plurality of air flow slots and engages the covering.

30. The method of claim 1, wherein when the covering is sealingly engaged to the outside surface of the rigid, breathable orthopedic cast a plurality of air flow channels are defined between the covering and the rigid, breathable orthopedic cast.

31. The method of claim 1, wherein the covering comprises two non-permeable layers wherein the first layer and the second layer are laminated and create a plurality of pockets of air trapped between the two layers.

32. A method of ventilating a rigid, breathable orthopedic cast comprising:

providing an air moving device, a non-porous cover comprising;
 a non porous membrane;
 an inner, cast-facing side comprising a plurality of protrusions disposed thereon that increase in size as the protrusions are spaced closer to the inlet;
 an outer side;
 a first and a second cover end, the first and second cover ends being free of the protrusions;
 an inlet for receiving an air moving device disposed about midway between the first cover end and the second cover end;
 a flange proximate the inlet adapted to engage an adapter; and
 at least two fastening straps comprising a hook and loop style fastening system;
sealingly engaging a first orthopedic cast end of an rigid, breathable orthopedic cast and a second orthopedic cast end of an orthopedic cast with the inner cast facing surface of the membrane wrapping around the first and second outside cast ends and wrapping at least partially around the opposite outer surface of the cover to sealingly engage the first and second outside orthopedic cast ends such that the cover is sealingly engaged to an outside surface of the rigid, breathable orthopedic cast;
engaging the air moving device to the inlet; and
utilizing the air moving device to move air through a first and a second inside end of the orthopedic cast, through the orthopedic cast and through the inlet in order to create a flow of air.

33. A method of ventilating a breathable, orthopedic cast comprising:
providing an orthopedic cast comprising an inner, porous material comprising at least one additive chosen from the group consisting of a scented component, a disinfectant, and a medicament and further providing an air moving device and a non-porous cover comprising:
 an inlet; and an inner, cast-facing side and an outer side, the inner, cast-facing side comprising a plurality of protrusions disposed thereon;
sealingly engaging an outside surface an orthopedic cast comprising a breathable material with the inner, cast-facing surface of the covering;
engaging the air moving device to the flange; and
utilizing the air moving device to move air into the cast, through the breathable material, and through the inlet such that the additive is actuated.

34. The method of claim 33, wherein the inlet comprises a flange for engaging an air moving device.

35. The method of claim 33, wherein the plurality of protrusions are pockets of air trapped between two layers of material.

* * * * *

UNITED STATES PATENT AND TRADEMARK OFFICE
CERTIFICATE OF CORRECTION

PATENT NO. : 7,497,838 B1
APPLICATION NO. : 11/726787
DATED : March 3, 2009
INVENTOR(S) : Dunagan It is certified that error appears in the above-identified patent and that said Letters Patent is hereby corrected as shown below:

Title Page; item (57);

Abstract, line 1;
    "sight" should be --site--

Column 1, line 25;
    "buildup" should be --build up--

Column 1, line 30;
    "sight" should be --site--

Column 2, line 45;
    "cross-elevated sectional" should be --cross-sectional, elevated--

Column 3, line 8;
    After "non-elastomeric" delete ","

Column 3, line 13;
    "or to due to" should be --or due to--

Column 3, line 36;
    After "adapter" delete "a"

Column 3, line 39;
    "positioned inlet 19" should be --positioned and inlet 19--

Column 3, line 54;
    "sight" should be --site--

Column 5, line 1;
    "aide" should be --aid--

Column 5, line 55;
    "protrusion's" should be --protrusions'--

Column 6, line 2;
    "special" should be --spatial--

UNITED STATES PATENT AND TRADEMARK OFFICE
CERTIFICATE OF CORRECTION

PATENT NO. : 7,497,838 B1
APPLICATION NO. : 11/726787
DATED : March 3, 2009
INVENTOR(S) : Dunagan It is certified that error appears in the above-identified patent and that said Letters Patent is hereby corrected as shown below:

Column 6, line 17;
"Figs. 7 and 11 adapter 18 typically" should be --As shown in Figs. 7 and 11, adapter 18 typically--

Column 7, line 56;
"sight" should be --site--

Column 10, claim 32, line 3;
"non porous" should be --non-porous--

Column 10, claim 32, line 19;
"cast facing" should be --cast-facing--

Column 10, claim 33, line 41;
"of" should have been added after --surface--

Signed and Sealed this

Eleventh Day of August, 2009

David J. Kappos
*Director of the United States Patent and Trademark Office*